(12) United States Patent
Ikeda et al.

(10) Patent No.: US 6,437,008 B1
(45) Date of Patent: Aug. 20, 2002

(54) AQUEOUS ORGANOPOLYSILOXANE EMULSION AND METHOD FOR THE PREPARATION THEREOF

(75) Inventors: Teruki Ikeda; Sachiko Yamada; Morizo Nakazato, all of Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 50 days.

(21) Appl. No.: 09/592,860

(22) Filed: Jun. 13, 2000

(30) Foreign Application Priority Data

Jun. 14, 1999 (JP) ............................. 11-166570

(51) Int. Cl.[7] ............. B01F 3/08; C08L 83/00; A61K 7/06; A61K 7/11
(52) U.S. Cl. ............ 516/57; 516/58; 516/67; 516/73; 516/74; 516/76; 516/924; 424/401; 424/70.12; 524/588
(58) Field of Search .............. 516/67, 924, 58, 516/57, 64, 73, 74, 76; 424/401, 70.12, 70.28; 510/122, 417; 524/588, 837, 838, 714, 745, 762

(56) References Cited

U.S. PATENT DOCUMENTS 6,238,656 B1 * 5/2001 Morita et al. ............ 424/70.12

FOREIGN PATENT DOCUMENTS

EP 798 332 A2 * 10/1997

* cited by examiner

*Primary Examiner*—Daniel S. Metzmaier
(74) *Attorney, Agent, or Firm*—Millen, White, Zelano & Branigan, P.C.

(57) ABSTRACT

Disclosed is an aqueous organopolysiloxane emulsion for use as an adjuvant to hair-care treatment toiletry preparations suitable in respect of the good storage stability and relatively large average diameter of the organopolysiloxane droplets of 0.1 to 1.0 mm despite the high viscosity of the organopolysiloxane and the high content of the organopolysiloxane. The organopolysiloxane emulsion consists of: (A) 70 to 90% by weight of an organopolysiloxane having a viscosity of $1 \times 10^5$ mPa·s or higher; (B) 1 to 15% by weight of a surface active agent; and (C) 5 to 25% by weight of water.

20 Claims, No Drawings

AQUEOUS ORGANOPOLYSILOXANE EMULSION AND METHOD FOR THE PREPARATION THEREOF

BACKGROUND OF THE INVENTION

The present invention relates to a novel aqueous organopolysiloxane emulsion useful as an adjuvant in various kinds of hair-care treatment toiletry preparations, polishing compositions, mold-release agents, fabric-finishing agents and the like as well as to a method for the preparation thereof.

While various toiletry preparations or, in particular, hair-care treatment compositions are conventionally compounded with an aqueous emulsion of an organopolysiloxane or silicone, it is usual that the emulsion is an aqueous emulsion of an organopolysiloxane having a high viscosity in view of good slippery feeling and high combing smoothness imparted to the hair treated therewith. Such an aqueous emulsion of a high-viscosity organopolysiloxane is prepared usually by using an anionic or non-ionic surface active agent when the intended application of the emulsion is an adjuvant to a shampoo composition. Japanese Patent Kokai 4-36226 and 4-243813 disclose a shampoo composition formulated with an aqueous emulsion of an organopolysiloxane, according to which a shampoo composition of excellent performance without a decrease in the foaming behavior can be obtained when the droplets of the organopolysiloxane dispersed in the aqueous medium have an average droplet diameter smaller than 2 $\mu$m. Japanese Patent Kokai 63-130512 and 5-163122 propose admixture of an aqueous emulsion of an organopolysiloxane in the form of a so-called microemulsion to a toiletry preparation. Further, Japanese Patent Kokai 7-188557 proposes use of an organopolysiloxane emulsion of which the dispersed droplets have a relatively large droplet diameter of 3 to 100 $\mu$m in view of the problem that an organopolysiloxane emulsion on the hair is readily washed away from the hair due to poor adhesion when the droplet diameter is relatively small as in the microemulsion mentioned above. The adhesion of an organopolysiloxane emulsion to the hair, however, can be further improved only when the droplet diameter of the organopolysiloxane is increased so much. On the other hand, it is accepted as desirable that an organopolysiloxane emulsion is prepared by using a cationic or non-ionic surface active agent when it is to be used as an adjuvant to a cationic hair-care treatment composition such as hair rinses, hair conditioners, hair treatment agents and the like.

Along with this line, Japanese Patent Kokai 9-316331 and 11-148010 propose an organopolysiloxane emulsion prepared by using a cationic surface active agent having an alkyl group of 16 or 18 carbon atoms, respectively. The organopolysiloxane droplets as the dispersed phase in these aqueous emulsions, however, have a droplet diameter of 10 to 30 $\mu$m. When the droplet diameter exceeds this range, the aqueous emulsion disadvantageously suffers a decrease in the storage stability because the emulsion is destroyed during storage. In addition, the content of the organopolysiloxane in these aqueous emulsions cannot exceed a range of 70 to 75% by because, when the content of the organopolysiloxane is larger than 75% by weight, the flowability of the aqueous emulsion is poor to cause inconvenience in handling.

Since an organopolysiloxane is in general a material having very low emulsifiability, an aqueous emulsion of an organopolysiloxane can usually be prepared only by giving a large quantity of mechanical energy using an emulsifying machine such as colloid mills, homogenizers, homomixers and the like. On the other hand, Japanese Patent Publication 4-49581 proposes a method for emulsification of an organopolysiloxane without using the above mentioned high-power emulsifying machines. This method, however, is a method for obtaining an aqueous emulsion of an organopolysiloxane having a relatively small droplet diameter with which combined use of a polyhydric alcohol is indispensable for emulsification. When the organopolysiloxane has a high viscosity, in particular, the above mentioned emulsifying machines are still insufficient for accomplishing full emulsification of such a high-viscosity organopolysiloxane so that proposals are made in Japanese Patent Kokai 7-173294 and 8-198969 on a method for the emulsification of a high-viscosity organopolysiloxane by using a special emulsifying machine capable of giving a high shearing force.

It is understood that, when a hair-care toiletry preparation is admixed with an aqueous emulsion of an organopolysiloxane, good improvements can be obtained in the deposition behavior of the organopolysiloxane to the hair and touch feeling and combing smoothness of the treated hair when the droplet diameter of the emulsified organopolysiloxane is relatively large. Further, the amount of the emulsion can be decreased with good handleableness when the concentration of the organopolysiloxane is high and the viscosity of the emulsion is low still with good storage stability of the emulsion. Further, it is desired to develop a method for efficiently emulsifying a high-viscosity organopolysiloxane by using a conventional general purpose stirrer machine without necessitating a special high-power emulsifying machine mentioned above which is indispensable in the prior art.

SUMMARY OF THE INVENTION

The present invention accordingly has an object to provide an aqueous emulsion of an organopolysiloxane having good storage stability despite the relatively large average diameter of the emulsified organopolysiloxane droplets in the range from 0.1 to 1.0 mm as well as to provide a method for the preparation of such an improved organopolysiloxane emulsion.

Thus, the aqueous emulsion of an organopolysiloxane, in which the average diameter of the emulsified organopolysiloxane droplets is in the range from 0.1 to 1.0 mm, comprises:

(A) from 70 to 90% by weight of (A-1) an organopolysiloxane having a viscosity of $1 \times 10^5$ mPa·s or higher at 25° C. represented by the average unit formula $R^1{}_a SiO_{(4-a)/2}$, in which $R^1$ is an unsubstituted or substituted monovalent hydrocarbon group having 1 to 20 carbon atoms and the subscript a is a positive number in the range from 1.8 to 2.2, or (A-2) a mixture consisting of (a) from 10 to 90% by weight of an organopolysiloxane having a viscosity of $1 \times 10^6$ mPa·s or higher at 25° C. represented by the average unit formula $R^1{}_a SiO_{(4-a)/2}$, in which $R^1$ is an unsubstituted or substituted monovalent hydrocarbon group having 1 to 20 carbon atoms and the subscript a is a positive number in the range from 1.8 to 2.2, and (b) from 90 to 10% by weight of an organopolysiloxane having a viscosity in the range from 10 to 1000 mm²/s at 25° C. represented by the average unit formula $R^1{}_a SiO_{(4-a)/2}$, in which $R^1$ is an unsubstituted or substituted monovalent hydrocarbon group having 1 to 20 carbon atoms and the subscript a is a positive number in the range from 1.8 to 2.2 or a hydrocarbon solvent having a boiling point in the range from 60 to 260° C.;

(B) from 1 to 15% by weight of a surface active agent selected from the group consisting of cationic surface active agents represented by the general formula $R^2_4N^+ \cdot X^-$, in which at least one of the four $R^2$ groups is an alkyl or alkenyl group having 12 to 22 carbon atoms, the rest of $R^2$ groups, if any, being an alkyl group having 1 to 5 carbon atoms or a benzyl group, and $X^-$ is a halogen ion or an organic anion, anionic surface active agents and non-ionic surface active agents; and (C) from 5 to 25% by weight of water as a solvent or dispersion medium of the components (A) and (B).

DETAILED DESCRIPTION OF THE PREFERRED EMBODIMENTS

The inventors have conducted extensive investigations with an object to solve the above described problems in the conventional organopolysiloxane emulsions of the prior art and have arrived at a discovery that an aqueous organopolysiloxane emulsion of a large average droplet diameter having good storage stability can; be obtained by agitating the above described components including (A) a specific organopolysiloxane, (B) a specific surface active agent and (C) water in a specific weight proportion by using a low-shearing stirrer, such as propeller mixers, anchor-blade mixers, paddle mixers, spiral ribbon mixers and the like, followed by dilution with water optionally containing a surface active agent leading to completion of the present invention on the base of this discovery.

In the average unit formulas representing the organopolysiloxanes as the component (A), the group denoted by $R^1$ is an unsubstituted or substituted monovalent hydrocarbon group having 1 to 20 carbon atoms exemplified by alkyl groups such as methyl, ethyl, propyl, butyl, pentyl, hexyl, heptyl, octyl nonyl, decyl, dodecyl, tetradecyl, hexadecyl and octadecyl groups, aryl groups such as phenyl and tolyl groups, cycloalkyl groups such as cyclopentyl and cyclohexyl groups, fluorinated alkyl groups such as 3,3,3-trifluoropropyl, 2-(perfluorobutyl)ethyl and 2-(perfluorooctyl)ethyl groups and amino-substituted alkyl groups such as 3-aminopropyl and 3-(N-2-aminoethylamino)-propyl groups as well as hydrocarbon groups substituted by one or more of other substituent groups such as epoxy groups, mercapto groups, acryloxy groups, (meth)acryloxy groups, aliphatic ester groups, carboxyl groups, hydroxyl groups, ether groups and the like, of which methyl, phenyl, and amino-substituted alkyl groups are; preferable. It is more preferable that at least 50% by moles of the groups denoted by $R^1$ are methyl groups.

It is essential in order for the hair-care treatment preparation compounded with the inventive organopolysiloxane emulsion to exhibit good deposition behavior of the organopolysiloxane on to the hair giving pleasant touch feeling that the organopolysiloxane as the component (A-1) has a viscosity of $1 \times 10^5$ mPa·s or higher or, preferably, $5 \times 10^5$ mPa·s or higher at 25° C. When the component (A) is a mixture of two organopolysiloxanes (a) and (b) in a specified weight proportion, the first organopolysiloxane (a) has a viscosity of $1 \times 10^6$ mPa·s or higher or, preferably, $5 \times 10^6$ mPa·s or higher at 25° C. while the second organopolysiloxane (b) has a viscosity in the range from 2 to 1000 mm²/s or preferably, from 10 to 500 mm²/s. When the viscosity of the second organopolysiloxane (b) is too low, the organopolysiloxane exhibits irritativeness to the human skin so that the organopolysiloxane emulsion is not suitable for use as an adjuvant in toiletry preparations while, when the viscosity of the organopolysiloxane (b) is too high, the miscibility thereof with the high-viscosity organopolysiloxane (a) is disadvantageously decreased.

The molecular structure of the low-viscosity organopolysiloxane (b) can be linear or cyclic. Examples of suitable cyclic organopolysiloxanes include hexamethyl cyclotrisiloxane, decamethyl cyclopentasiloxane, dodecamethyl cyclohexasiloxane, 1,3,5-trimethyl-1,3,5-tri(3,3,3-trifluoropropyl) cyclotrisiloxane and 1,3,5,7-tetramethyl-1,3,5,7-tetra(3,3,3-trifluoropropyl) cyclotetrasiloxane, of which decamethyl cyclopentasiloxane and dodecamethyl cyclohexasiloxane are particularly preferable.

The above described low-viscosity organopolysiloxane as the component (b) can alternatively be replaced with a hydrocarbon solvent having a boiling point in the range from 60 to 260° C. When the boiling point of the hydrocarbon solvent is too low, the organopolysiloxane emulsion containing such a hydrocarbon solvent emits an unpleasant odor so that the emulsion is not suitable as an adjuvant to toiletry preparations while, when the boiling point of the hydrocarbon solvent is too high, the miscibility thereof with the high-viscosity organopolysiloxane as the component (a) is undesirably decreased.

A variety of commercial products of hydrocarbon solvents suitable for use in the present invention as the component (b) are available on the market including Isopars C, E, G, H, L and M (each a product by Exxon Co.), IP Solvents 1016, 1620 and 2028 (each a product by Idemitsu Petrochemical Co.), Marukasol R (a product by Maruzen Petrochemical Co.), Nisseki Isosols 300 and 400 (each a product by Nippon Petrochemical Co.), Shellsol 71 (a product by Shell Chemical Co.), Solutols 100, 130 and 220 (each a product by Philips Co.) and isohexadecane (a product by Baeyer Japan Co.).

It is preferable that the mixture of two organopolysiloxanes (a) and (b) has a viscosity of $1 \times 10^4$ mPa·s or higher at 25° C. A viscosity lower than $1 \times 10^4$ mPa·s means that the weight proportion of the high-viscosity organopolysiloxane (a) in the mixture is not large enough so that the aqueous emulsion comprising the mixture of organopolysiloxanes is not suitable for use as an adjuvant in a hair-care treatment toiletry preparation. When each of the organopolysiloxanes (a) and (b) is a dimethylpolysiloxane, it is desirable that the mixture of the two has a viscosity of $1 \times 10^5$ mPa·s or higher at 25° with an increased weight proportion of the high-viscosity organopolysiloxane as the component (a).

The cationic surface active agent which can be the component (B) in the inventive emulsion composition is a quaternary ammonium compound represented by the general formula $R^2_4N^+ \cdot X^-$, in which at least one of the four $R^2$ groups is an alkyl or alkenyl group having 12 to 22 carbon atoms, the remainder of the groups $R^2$, if any, being an alkyl group of 1 to 5 carbon atoms, and $X^-$ is a halogen anion or an organic anion. Examples of the quaternary ammonium, salt compound suitable as the component (B) in the inventive emulsion include lauryl trimethylammonium chloride, cetyl trimethylammonium chloride, stearyl trimethylammonium chloride, distearyl dimethylammonium chloride, behenyl trimethylammonium chloride, lauryl trimethylammonium methosulfate, cetyl trimethylammonium methosulfate, and stearyl trimethylammonium methosulfate.

The component (B) can also be an anionic surface active agent which is exemplified by alkyl sulfates, alkylbenzenesulfonates, alkylsulfonates, alkylnaphthalenesulfonates, dialkylsulfosuccinates, polyoxyethylene aliphatic alcohol ether sulfates, polyoxyethylene alkyl ether sulfates, polyoxyethylene alkylphenyl ether sulfates, polyoxyethylene alkylphosphates and polyoxyethylene alkylphenylphosphates.

The component (B) can further be a non-ionic surface active agent which is exemplified by polyoxyethylene alkyl ethers, polyoxyethylene-polyoxypropylene alkyl ethers, polyoxyethylene alkylphenyl ethers, polyethyleneglycol fatty acid esters, sorbitan fatty acid esters, polyoxyethylene sorbitan fatty acid esters, polyoxyethylene sorbitol fatty acid esters, glycerin fatty acid esters, polyoxyethylene glycerin fatty acid esters, polyglycerin fatty acid esters and propyleneglycol fatty acid esters.

The weight proportion of the above described component (B) in the inventive aqueous emulsion is in the range from 1 to 15% by weight or, preferably, from 3 to 10% by weight. When the amount of the component (B) is too small, an aqueous emulsion having good stability can hardly be obtained while, when the amount thereof is too large, the organopolysiloxane emulsion obtained therewith has an unduly high viscosity to cause inconvenience in handling in addition to the problem that the hair-care treatment toiletry preparation compounded with such an organopolysiloxane emulsion may suffer stickiness of the hair treated therewith.

The weight proportion of the component (A), i.e. the organopolysiloxane, component (B), i.e. the surface active agent, and component (C), i.e. water, in the inventive organopolysiloxane emulsion are from 70 to 90% or, preferably, from 75 to 85% of the component (A), from 1 to 15% or, preferably, from 3 to 10% of the component (B) and from 5 to 25% or, preferably, from 10 to 20% of the component (C). When the weight proportion of the component (A) is too high, a stable aqueous emulsion can hardly be obtained. When the weight proportion of the component (C) is too low, a stable aqueous emulsion can also be hardly obtained although the amount of water should be as small as possible in order to obtain an increased content of the effective ingredients.

The organopolysiloxane droplets as the dispersed phase in the inventive aqueous emulsion have an average particle (diameter in the range from 0.1 to 1.0 mm or, preferably, from 0.1 to 0.5 mm. When the average diameter of the organopolysiloxane droplets is too small, the adherence behavior of the organopolysiloxane to the hair is decreased while, when the average droplet diameter is too large, the emulsion suffers a decrease in the stability.

In the preparation of the inventive aqueous organopolysiloxane emulsion, a blend is first prepared from 70 to 90 parts by weight of the organopolysiloxane as the component (A), from 1 to 15 parts by weight of the surface active agent as the component (B) and from 5 to 25 parts by weight of water as the component (C). It is convenient and preferable in this case that the component (B) is first dissolved in the component (C) to form a uniform aqueous solution of the surface active agent to which the component (A) is added and emulsified therein.

In the next place, the blend of the components (A), (B) and (C) is agitated at a temperature of 0 to 50 C for 1 to 4 hours to effect emulsification of the component (A) under a relatively low shearing force by using a suitable stirrer machine such as propeller mixers, paddle mixers, anchor-blade mixers and the like.

Finally, though optional, the above obtained aqueous emulsion is diluted by adding water or an aqueous solution of a surface active agent to accomplish the target weight proportions of the respective components which should be (A):(B):(C)=(70–90):(1–15):(5–25) or, preferably, (75–85): (3–10): (10–20).

In the following, the aqueous organopolysiloxane emulsion of the present invention is described in more detail by way of examples, in which the values of viscosity are all those obtained by the measurement at 25° C. and the term of "parts" always refers to "parts by weight".

The organopolysiloxane emulsions prepared in the Examples described below were evaluated by measuring the viscosity and the average droplet diameter using a particle size analyzer (Model Coulter Multisizer II, manufactured by Coulter Electronics Co.) and by testing the stability when a 100 g portion of the emulsion was taken in a hermetically sealable glass bottle and kept standing at 45° C. for 30 days to record the condition of the emulsion in three ratings of: "A" for absolute absence of separation into phases; "B" for slight separation into phases; and "C" for complete separation into phases.

Preparation 1.

An organopolysiloxane mixture, referred to as the mixture 1 hereinafter, having a viscosity of $5.0\times10^5$ mPa·s was prepared by uniformly mixing a first dimethylpolysiloxane having a viscosity of $1.5\times10^7$ mPa·s and a second dimethylpolysiloxane having a viscosity of 200 mm$^2$/s in a weight proportion of 40:60.

Preparation 2.

Another organopolysiloxane mixture, referred to as the mixture 2 hereinafter, having a viscosity of $8.0\times10^5$ mPa·s was prepared by uniformly mixing a third dimethylpolysiloxane having a viscosity of $2.0\times10^7$ mPa·s and a fourth dimethylpolysiloxane having a viscosity of 20 mm$^2$/s in a weight proportion of 40:60.

Example 1.

A separable flask of 10 liter capacity equipped with a glass-made anchor-blade stirrer was charged with 80 parts of the mixture 1, 4.8 parts of cetyl trimethylammonium chloride and 11.2 parts of purified water and they were agitated together for 2 hours by driving the stirrer at 80 rpm to obtain a base aqueous emulsion of the mixture 1, which was diluted by the addition of a solution of 1.2 parts of cetyl trimethylammonium chloride in 2.8 parts of purified water under gentle agitation with the stirrer driven at 30 rpm.

The thus obtained aqueous emulsion had an average droplet diameter of 0.11 mm and a viscosity of 2400 mPa·s. The stability of the emulsion on standing was rated A.

Example 2.

The procedure for the preparation of an aqueous organopolysiloxane emulsion was substantially the same as in Example 1 except that the base emulsion was prepared from 75 parts of the mixture 2, 4.5 parts of stearyl trimethylammonium chloride and 10.5 parts of purified water and the base emulsion was diluted by the addition of a solution of 3.0 parts of stearyl trimethylammonium chloride in 7.0 parts of purified water.

The thus obtained aqueous emulsion had an average droplet diameter of 0.12 mm and a viscosity of 1500 mPa·s. The stability of the emulsion on standing was rated A.

Example 3.

The procedure for the preparation of an aqueous organopolysiloxane emulsion was substantially the same as in Example 1 except that the base emulsion was prepared from 80 parts of a dimethylpolysiloxane having a viscosity of $1\times10^6$ mPa·s, 4.8 parts of stearyl trimethylammonium chloride and 11.2 parts of purified water and the base emulsion was diluted by the addition of a solution, of 1.2 parts of stearyl trimethylammonium chloride in 2.8 parts of purified water.

The thus obtained aqueous emulsion had an average droplet diameter of 0.12 mm and a viscosity of 2500 mPa·s.

The stability of the emulsion on standing was rated A.

Example 4.

The procedure for the preparation of an aqueous organopolysiloxane emulsion was substantially the same as in Example 1 for the preparation of the base emulsion except that the emulsion was prepared from 75 parts of the mixture 1, 7.5 parts of cetyl trimethylammonium chloride and 17.5 parts of purified water and the base emulsion was diluted by the addition of a solution of 1.2 parts of stearyl trimethylammonium chloride in 2.8 parts of purified water and the emulsion was not diluted any further.

The thus obtained aqueous emulsion had an average droplet diameter of 0.60 mm and a viscosity of 700 mPa·s. The stability of the emulsion on standing was rated B.

Example 5.

The procedure for the preparation of an aqueous organopolysiloxane emulsion was substantially the same as in Example 1 except that the base emulsion was prepared from 75 parts of the mixture 2, 5.0 parts of a polyoxyethylene (3 moles addition) alkyl ether sulfate and 15.0 parts of purified water and the base emulsion was diluted by the addition of a solution of 1.25 parts of the same surface active agent as above and 0.1 part of phenoxyethyl alcohol in 3.75 parts of purified water.

The thus obtained aqueous emulsion had an average droplet diameter of 0.10 mm and a viscosity of 6000 mPa·s. The stability of the emulsion on standing was rated A.

Example 6.

The procedure for the preparation of an aqueous organopolysiloxane emulsion was substantially the same as in Example 1 except that the base emulsion was prepared from 80 parts of the mixture 1, 2.0 parts of a polyoxyethylene (20 moles addition) sorbitan monolaurate, 3.0 parts of a polyoxyethylene (3 moles addition) alkyl ether sulfate and 15.0 parts of purified water and the base emulsion was diluted by the addition of a solution of 1.0 part of the polyoxyethylene (20 moles addition) sorbitan monolaurate and 0.1 part of phenoxyethyl alcohol in 4.0 parts of purified water.

The thus obtained aqueous emulsion had an average droplet diameter of 0.11 mm and a viscosity of 5000 mPa·s. The stability of the emulsion on standing was rated A.

Comparative Example 1.

The procedure for the preparation of an aqueous organopolysiloxane emulsion was substantially the same as in Example 4 except that the emulsion was prepared from 70 parts of the mixture 1, 8.4 parts of stearyl trimethylammonium chloride and 21.6 parts of purified water without further dilution.

The thus obtained aqueous emulsion had an average droplet diameter of 1.1 mm and a viscosity of 500 mPa·s. The stability of the emulsion on standing was rated C.

Comparative Example 2.

The procedure for the preparation of an aqueous organopolysiloxane emulsion was substantially the same as in Example 4 except that the emulsion was prepared from 70 parts of the same high viscosity dimethylpolysiloxane as used in Example 3, 8.4 parts of stearyl trimethylammonium chloride and 21.6 parts of purified water without further dilution.

The thus obtained aqueous emulsion had an average droplet diameter of 1.3 mm and a viscosity of 480 mPa·s. The stability of the emulsion on standing was rated C.

What is claimed is:

1. An aqueous emulsion of an organopolysiloxane comprising:
   (A) 70 to 90% by weight based on the emulsion of either component (A-1) or component (A-2), wherein
   (A-1) is an organopolysiloxane having a viscosity of $1 \times 10^5$ mPa·s or higher at 25° C. represented by the average unit formula $R^1_a SiO_{(4)/2}$, in which $R^1$ is an unsubstituted or substituted monovalent hydrcarbon group having from 1 to 20 carbon atoms and subscript a is a positive number from 1.8 to 2.2, and
   (A-2) is a mixture of
      (a) 10 to 90% by weight of said mixture of an organopolysiloxane having a viscosity of $1 \times 10^6$ mPa·s or higher at 25° C. represented by the average unit formula $R^1_a SiO_{(4-a)/2}$, in which $R^1$ is an unsubstituted or substituted monovalent hydrcarbon group having from 1 to 20 carbon atoms and subscript a is a positive number from 1.8 to 2.2, and
      (b) 90 to 10% by weight of said mixture of an organopolysiloxane having a viscosity of 10 to 1000 mm²/s at 25° C. represented by the average unit formula $R^1_a SiO_{(4-a)/2}$, in which $R^1$ is an unsubstituted or substituted monovalent hydrcarbon group having from 1 to 20 carbon atoms and subscript a is a positive number from 1.8 to 2.2 or a hydrocarbon solvent having a boiling point in the range from 60 to 260° C.;
   (B) 1 to 15% by weight based on the weight of the emulsion of a surface active agent selected from the group consisting of
   anionic surface active agents,
   nonionic surface active agents, and
   cationic surface active agents, wherein said cationic surface active agents are represented by the formula $R^2_4 N^+ X^-$, in which at least one of the four $R^2$ groups is an alkyl or alkenyl group having 12 to 22 carbon atoms, the rest of the $R^2$ groups, if any, are each an alkyl group having 1 to 5 carbon atoms or a benzyl group, and $X^-$ is a halogen ion or an organic anion; and
   (C) 5 to 25% by weight based on the weight of the emulsion of water as a solvent or dispersion medium of the components (A) and (B), wherein the average diameter of the emulsified organopolysiloxane droplets is 0.11 to 1.0 mm.

2. An aqueous emulsion according to claim 1, in which at least 50% by moles of the groups denoted by $R^1$ are methyl groups.

3. An aqueous emulsion according to claim 1, in which the organopolysiloxane of component (A-1) has a viscosity of $5 \times 10^5$ mPa·s or higher at 25° C.

4. An aqueous emulsion according to claim 1, in which the organopolysiloxane of component (a) has a viscosity of $5 \times 10^6$ mPa·s or higher at 25° C.

5. An aqueous emulsion according to claim 1, in which the organopolysiloxane of component (b) has a viscosity in the range from 10 to 500 mm²/s at 25° C.

6. An aqueous emulsion according to claim 1, in which the mixture of the organopolysiloxanes of component (a) and the organopolysiloxane of component (b) has a viscosity of $1 \times 10^4$ mPa·s or higher at 25° C.

7. An aqueous emulsion according to claim 1, in which the weight proportions of the components (A), (B), and (C) are 75 to 85%, 3 to 10%, and 10 to 20%, respectively based on the weight of the emulsion.

8. An aqueous emulsion according to claim 1, in which the average diameter of the organopolysiloxane droplets is 0.11 to 0.5 mm.

9. An aqueous emulsion according to claim 1, wherein $R^1$ is a monovalent hydrocarbon group optionally substituted by fluorine, amino, epoxy, mercapto, acryloxy, (meth) acryloxy, aliphatic ester, carboxyl, hydroxyl, or ether groups.

10. An aqueous emulsion according to claim 1, wherein $R^1$ is methyl, ethyl, propyl, butyl, pentyl, hexyl, heptyl, octyl, nonyl, decyl, dodecyl, tetradecyl, hexadecyl, octadecyl, phenyl, tolyl, cyclopentyl, cyclohexyl, 3,3,3-trifluoropropyl, 2-(perfluorobutyl)ethyl, 2-(perfluorooctyl) ethyl, 3-aminopropyl, or 3-(N-2-aminoethylamino)-propyl.

11. An aqueous emulsion according to claim 4, in which the organopolysiloxane of component (b) has a viscosity of 10 to 500 mm²/s at 25° C.

12. An aqueous emulsion according to claim 1, wherein the organopolysiloxane of component (b) is hexamethyl cyclotrisiloxane, decamethyl cyclopentasiloxane, dodecamethyl cyclohexasiloxane, 1,3,5-trimethyl-1,3,5-tri-(3,3,3-trifluoropropyl) cyclotrisiloxane or 1,3,5,7-tetramethyl-1,3,5,7-tetra(3,3,3-trifluoropropyl) cyclotetrasiloxane.

13. An aqueous emulsion according to claim 1, wherein component (b) is a hydrocarbon solvent having a boiling point of 60° C. to 260° C.

14. An aqueous emulsion according to claim 1, wherein component (A-2) is a mixture of organopolysiloxane (a) and organopolysiloxane (b) having a viscosity of $1 \times 10^4$ mPa·s or higher at 25° C.

15. An aqueous emulsions according to claim 1, wherein component (B) is:

a quaternary ammonium salt selected from the group consisting of lauryl trimethylammonium chloride, cetyl trimethylammonium chloride, stearyl trimethylammonium chloride, distearyl dimethylammonium chloride, behenyl trimethylammonium chloride, lauryl trimethylammonium methosulfate, cetyl trimethylammonium methosulfate, stearyl trimethylammonium methosulfate;

an anionic surface active agent selected from the group consisting of alkyl sulfates, alkylbenzenesulfonates, alkylsulfonates, alkylnaphthalenesulfonates, dialkylsulfosuccinates, polyoxyethylene aliphatic alcohol ether sulfates, polyoxyethylene alkyl ether sulfates, polyoxyethylene alkylphenyl ether sulfates, polyoxyethylene alkylphosphates and polyoxyethylene alkylphenylphosphates; or a non-ionic surface active agent selected from the group consisting of polyoxyethylene alkyl ether, polyoxyethylene-polyoxypropylene alkyl ether, polyoxyethylene alkylphenyl ether, polyethyleneglycol fatty acid esters, sorbitan fatty acid esters, polyoxyethylene sorbitan fatty acid esters, polyoxyethylene sorbitol fatty acid esters, glycerin fatty acid esters, polyoxyethylene glycerin fatty acid esters, polyglycerin fatty acid esters and propyleneglycol fatty acid esters.

16. An aqueous emulsion according to claim 1, wherein said emulsion contains 3–10% by weight of component (B).

17. An aqueous emulsion according to claim 1, wherein the average diameter of the emulsified organopolysiloxane droplets is 0.12 to 1.0 mm.

18. A process for preparing an aqueous emulsion composition according to claim 1, comprising:

preparing a blend containing 70–90 parts by weight of the organopolysiloxane of component (A), 1 to 15 parts by weight of the surface active agent component (B) and 5 to 25 parts by weight of water as component (C);

agitating the blend of components (A), (B) and (C) at a temperature of 0° C. to 50° C. for one to four hours under sheering force using a propeller mixer, paddle mixer or anchor-blade mixer, whereby an aqueous emulsion of organopolysiloxane is obtained wherein the average diameter of the emulsified organopolysiloxane droplets is 0.11 to 1.0 mm.

19. An aqueous emulsions according to claim 10, wherein component (B) is: a quaternary ammonium salt selected from the group consisting of lauryl trimethylammonium chloride, cetyl trimethylammonium chloride, stearyl trimethylammonium chloride, distearyl dimethylammonium chloride, behenyl trimethylammonium chloride, lauryl trimethylammonium methosulfate, cetyl trimethylammonium methosulfate, stearyl trimethylammonium methosulfate;

an anionic surface active agent selected from the group consisting of alkyl sulfates, alkylbenzenesulfonates, alkylsulfonates, alkylnaphthalenesulfonates, dialkylsulfosuccinates, polyoxyethylene aliphatic alcohol ether sulfates, polyoxyethylene alkyl ether sulfates, polyoxyethylene alkylphenyl ether sulfates, polyoxyethylene alkylphosphates and polyoxyethylene alkylphenylphosphates; or a non-ionic surface active agent selected from the group consisting of polyoxyethylene alkyl ether, polyoxyethylene-polyoxypropylene alkyl ether, polyoxyethylene alkylphenyl ether, polyethyleneglycol fatty acid esters, sorbitan fatty acid esters, polyoxyethylene sorbitan fatty acid esters, polyoxyethylene sorbitol fatty acid esters, glycerin fatty acid esters, polyoxyethylene glycerin fatty acid esters, polyglycerin fatty acid esters and propyleneglycol fatty acid esters.

20. An aqueous emulsion according to claim 1, wherein the surface active agent component (B) is selected from cationic agents represented by the formula $R^2_4N^+ \cdot X^-$, in which al least one of the four $R^2$ groups is an alkyl or alkenyl group having 12 to 22 carbon atoms, the rest of the $ER^2$ groups, if any, are each an alkyl group having 1 to 5 carbon atoms or a benzyl group, and $X^-$ is a halogen ion or an organic anion.

* * * * *